United States Patent
Zadno-Azizi et al.

(10) Patent No.: US 6,632,243 B1
(45) Date of Patent: Oct. 14, 2003

(54) BODY FLUID FLOW CONTROL DEVICE

(75) Inventors: Gholam-Reza Zadno-Azizi, Newark, CA (US); John S. Ford, Manhattan Beach, CA (US); April Marano-Ford, Manhattan Beach, CA (US)

(73) Assignee: Emphasys Medical Inc., Redwood City, CA (US)

( * ) Notice: Subject to any disclaimer, the term of this patent is extended or adjusted under 35 U.S.C. 154(b) by 0 days.

(21) Appl. No.: 09/397,218

(22) Filed: Sep. 16, 1999

Related U.S. Application Data

(63) Continuation of application No. 08/931,552, filed on Sep. 16, 1997, now Pat. No. 5,954,766.

(51) Int. Cl.[7] .................................................. A61F 2/06
(52) U.S. Cl. .................. 623/1.24; 623/23.68; 623/23.7; 606/191; 606/194
(58) Field of Search ................................ 606/191–195, 606/197–198; 604/65–67; 600/29–32; 623/1.11, 1.12, 1.2, 1.24, 1.18–1.19, 2.14, 2.18, 2.17, 2.28, 900, 1.13, 1.25, 1.26, 1.32–1.33, 23.64–23.7

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,788,327 A | 1/1974 | Donowitz et al. | 128/350 |

(List continued on next page.)

FOREIGN PATENT DOCUMENTS

| | | | | |
|---|---|---|---|---|
| DE | WO 96/34582 | * | 11/1996 | A61F/2/48 |
| EP | 0621 015 B1 | | 10/1994 | |
| EP | 000621015 | | 10/1994 | 623/1 |

(List continued on next page.)

OTHER PUBLICATIONS

Brochure re "Authocath 100—Physician Brochure" and "Abstract" (date unknown).

Al Jishi et al., "Selective Bronchial Occlusion for Treatment of Bullous Interstitial Emphysema and Bronchopleural Fistula." *J. of Pediatric Surgery,* 29:1545–1547, 1994.

Derwent citing Soviet Union Patent No. SU 852–321, published Jul. 8, 1981, for: "Treatment for acute pulmonary and pleural disease in children—by pneumo–abcessotomy simultaneous with occlusion of affected lung part".

Harris et al., "The Experimental Production in Dogs of Emphysema with Associated Asthmatic Syndrome by Means of an Intratracheal Ball Valve", *J. Lab. Clini. Med.,* 9(iv):75–88, 1919.

Lewis et al., "Pulmonary Interstitial Emphysema: Selective Broncial Occlusion with a Swan–Ganz Catheter", *Archives of Disease in Childhood,* 63:313–315, 1988.

(List continued on next page.)

*Primary Examiner*—David J. Isabella
*Assistant Examiner*—Urmi Chattopadhyay
(74) *Attorney, Agent, or Firm*—Heller Ehrman White & McAuliffe

(57) ABSTRACT

A device to provide body fluid flow control in the form of a valve to be located within a duct or passageway. The device is controlled through pressure above a preselected threshold. Bulk resilience about a passageway in a valve body provides the mechanism for controlled flow. One-way valve operation may be provided through a flap or through a pressure differential on the valve body depending upon the direction of flow. A frame structure positioned within a resilient seal includes longitudinally elongate elements which may be of spring material, malleable material or heat recoverable material so as to accomplish an initial insertion state and an expanded anchoring state. A valve support transitions between the resilient seal portion and the valve body to insure that the states do not change the threshold opening pressure. Insertion devices may be employed to position and actuate a change of state of the frame in the body duct or passageway.

10 Claims, 6 Drawing Sheets

U.S. PATENT DOCUMENTS

| | | | |
|---|---|---|---|
| 3,874,388 A | 4/1975 | King et al. ................. | 128/334 |
| 4,014,318 A | 3/1977 | Dockum et al. ............... | 128/1 |
| 4,086,665 A | 5/1978 | Poirier .......................... | 623/1 |
| 4,212,463 A | 7/1980 | Repinski et al. ............ | 273/418 |
| 4,302,854 A | 12/1981 | Runge ............................. | 3/1.7 |
| 4,710,192 A | 12/1987 | Liotta et al. ................... | 623/1 |
| 4,732,152 A | 3/1988 | Wallsten et al. ............ | 128/343 |
| 4,759,758 A | 7/1988 | Gabbay ........................ | 623/2 |
| 4,795,449 A | 1/1989 | Schneider et al. .......... | 604/329 |
| 4,808,183 A | 2/1989 | Panje ............................. | 623/9 |
| 4,819,664 A | 4/1989 | Nazari ................. | 128/207.15 |
| 4,830,003 A | 5/1989 | Wolff et al. ................. | 128/343 |
| 4,832,680 A | 5/1989 | Haber et al. .................. | 600/31 |
| 4,846,836 A | 7/1989 | Reich .......................... | 623/11 |
| 4,850,999 A | 7/1989 | Planck .......................... | 623/1 |
| 4,852,568 A | 8/1989 | Kensey ....................... | 128/325 |
| 4,877,025 A | 10/1989 | Hanson ................ | 128/107.16 |
| 4,934,999 A | 6/1990 | Bader ........................... | 600/29 |
| 4,968,294 A | 11/1990 | Salama ......................... | 600/30 |
| 5,061,274 A | 10/1991 | Kensey ....................... | 606/213 |
| 5,116,360 A | 5/1992 | Pinchuk et al. ................ | 623/1 |
| 5,116,564 A | 5/1992 | Jansen et al. ............... | 264/255 |
| 5,123,919 A | 6/1992 | Sauter et al. .................. | 623/2 |
| 5,151,105 A | 9/1992 | Kwan-Gett ................... | 623/1 |
| 5,161,524 A | 11/1992 | Evans .................. | 128/203.15 |
| 5,306,234 A | 4/1994 | Johnson ....................... | 604/49 |
| 5,352,240 A | 10/1994 | Ross ............................. | 623/2 |
| 5,358,518 A | 10/1994 | Camilli ......................... | 623/2 |
| 5,366,478 A | 11/1994 | Brinkerhoff et al. ........ | 660/213 |
| 5,382,261 A | 1/1995 | Palmaz ....................... | 606/158 |
| 5,409,019 A | 4/1995 | Wilk .......................... | 128/898 |
| 5,411,552 A | 5/1995 | Andersen et al. ............. | 623/2 |
| 5,413,599 A | 5/1995 | Imachi et al. .................. | 623/2 |
| 5,417,226 A | 5/1995 | Juma ......................... | 128/885 |
| 5,445,626 A | 8/1995 | Gigante ...................... | 604/349 |
| 5,499,995 A | 3/1996 | Teirstein ..................... | 606/192 |
| 5,500,014 A | 3/1996 | Quijano et al. ................ | 623/2 |
| 5,645,565 A | 7/1997 | Rudd et al. ................. | 606/213 |
| 5,660,175 A | 8/1997 | Dayal ................... | 128/207.15 |
| 5,662,713 A | 9/1997 | Andersen et al. ............ | 623/12 |
| 5,683,451 A | 11/1997 | Lenker et al. ................. | 623/1 |
| 5,697,968 A | 12/1997 | Rogers et al. ................. | 623/1 |
| 5,755,770 A | 5/1998 | Ravenscroft ................... | 623/1 |
| 5,800,339 A | 9/1998 | Salama ........................ | 600/29 |
| 5,840,081 A | 11/1998 | Andersen et al. ............. | 623/2 |
| 5,851,232 A | 12/1998 | Lois ............................. | 623/1 |
| 5,855,587 A | 1/1999 | Hyon et al. ................. | 606/188 |
| 5,855,597 A | 1/1999 | Jayaraman .................... | 623/1 |
| 5,855,601 A | 1/1999 | Bessler et al. ................. | 623/2 |
| 5,944,738 A | 8/1999 | Amplatz et al. ............ | 606/213 |
| 5,947,997 A | 9/1999 | Pavcnik et al. ............. | 606/213 |
| 5,954,766 A | 9/1999 | Zadno-Azizi et al. .......... | 623/2 |
| 5,957,949 A | 9/1999 | Leonhardt et al. .......... | 606/213 |
| 5,976,174 A | 11/1999 | Ruiz .......................... | 606/213 |
| 5,984,965 A | 11/1999 | Knapp et al. ................. | 623/12 |
| 6,007,575 A | 12/1999 | Samuels ........................ | 623/1 |
| 6,020,380 A | 2/2000 | Killian ........................ | 514/570 |
| 6,027,525 A | 2/2000 | Suh et al. ........................ | 623/1 |
| 6,051,022 A | 4/2000 | Cai et al. ....................... | 623/2 |
| 6,068,638 A | 5/2000 | Makower .................... | 606/159 |
| 6,077,291 A | 6/2000 | Das ............................. | 606/213 |
| 6,083,255 A | 7/2000 | Laufer et al. ................. | 607/96 |
| 6,123,663 A | 9/2000 | Rebuffat ...................... | 600/37 |
| 6,135,729 A | 10/2000 | Aber ......................... | 417/420 |
| 6,135,991 A | 10/2000 | Muni et al. ................. | 604/509 |
| 6,162,245 A | 12/2000 | Jayaraman ................. | 623/1.15 |
| 6,168,614 B1 | 1/2001 | Andersen et al. .............. | 623/1 |
| 6,174,323 B1 | 1/2001 | Biggs et al. ................. | 606/232 |
| 6,183,520 B1 * | 2/2001 | Pintauro et al. .............. | 600/29 |
| 6,200,333 B1 | 3/2001 | Laufer ........................ | 607/96 |
| 6,206,918 B1 | 3/2001 | Campbell et al. .......... | 623/2.32 |
| 6,234,996 B1 | 5/2001 | Bagaoisan et al. ........ | 604/97.01 |
| 6,245,102 B1 | 6/2001 | Jayaraman ................. | 623/1.15 |
| 6,258,100 B1 | 7/2001 | Alferness et al. ........... | 606/108 |
| 6,270,527 B1 | 8/2001 | Campbell et al. ........... | 623/2.18 |
| 6,287,290 B1 | 9/2001 | Perkins et al. .............. | 604/516 |
| 6,293,951 B1 | 9/2001 | Alferness et al. ............ | 606/108 |
| 6,302,893 B1 | 10/2001 | Limon et al. ............... | 606/108 |
| 6,312,407 B1 | 11/2001 | Zadno-Azizi et al. .. | 604/103.03 |
| 6,325,777 B1 | 12/2001 | Zadno-Azizi et al. .... | 604/97.01 |
| 6,325,778 B1 | 12/2001 | Zadno-Azizi et al. .... | 604/99.02 |
| 6,327,772 B1 | 12/2001 | Zadno-Azizi et al. ......... | 29/557 |
| 6,355,014 B1 | 3/2002 | Zadno-Azizi et al. .... | 604/99.02 |
| 2001/0037808 A1 | 11/2001 | Deem et al. ........... | 128/200.24 |
| 2002/0077696 A1 | 6/2002 | Zadno-Azizi et al. ...... | 623/1.24 |
| 2002/0095209 A1 | 7/2002 | Zadno-Azizi et al. ...... | 623/1.24 |

FOREIGN PATENT DOCUMENTS

| | | | |
|---|---|---|---|
| EP | 1 078 601 A2 | 2/2001 | |
| GB | 2 324 729 | 4/1998 | |
| SU | 852321 | 7/1981 | |
| SU | 1371700 | 2/1988 | .................... 623/2 |
| SU | 1593651 | 9/1990 | .................... 623/1 |
| WO | 94/26175 | 11/1994 | |
| WO | 95/32018 | 11/1995 | |
| WO | 97/44085 | 11/1997 | |
| WO | 98/00840 | 1/1998 | |
| WO | 98/19633 | 5/1998 | |
| WO | 98/39047 | 9/1998 | |
| WO | 98/44854 A1 | 10/1998 | |
| WO | 98/48706 | 11/1998 | |
| WO | 99/01076 | 1/1999 | |
| WO | 99/13801 | 3/1999 | |
| WO | 99/26692 | 6/1999 | |
| WO | 99/32040 | 7/1999 | |
| WO | 99/42059 | 8/1999 | |
| WO | 99/42161 | 8/1999 | |
| WO | 00/42950 | 7/2000 | |
| WO | 00/51510 | 9/2000 | |
| WO | 00/62699 | 10/2000 | |
| WO | 00/78386 A1 | 12/2000 | |
| WO | 01/02042 A1 | 1/2001 | |
| WO | 01/03642 A1 | 1/2001 | |
| WO | 01/05334 A1 | 1/2001 | |
| WO | 01/10313 A1 | 2/2001 | |
| WO | 01/10314 A2 | 2/2001 | |
| WO | 01/12104 A1 | 2/2001 | |
| WO | 01/13839 A1 | 3/2001 | |
| WO | 01/13908 A2 | 3/2001 | |
| WO | 01/45590 A2 | 6/2001 | |
| WO | 01/49213 A2 | 7/2001 | |
| WO | 01/54625 A1 | 8/2001 | |
| WO | 01/66190 A2 | 9/2001 | |
| WO | 01/87170 A1 | 11/2001 | |
| WO | 02/22072 A2 | 3/2002 | |

OTHER PUBLICATIONS

Mathew et al., "Selective bronchial obstruction for treatment of bullous interstitial emphysema." *J. of Ped.*, 96:475–477, 1980.

Okada et al., "Emergent Bronchofiberoptic Bronchial Occlusion for Intractable Pneumothorax with Sever Emphysema" *The Jap. J. of Thor. And Cardio. Sur.*, 46:1078–1081, 1998.

Puhakka et al., "Acute Bronchial Obstruction: An Experimental Rabbit Model Study." *Int. J. of Pediatric Otorhinolaryngology*, 18:107–118, 1989.

Snider et al., *The Definition of Emphysema*: Report of the National Heart Lung and Blood Institute, Division of Lung Diseases Workshop, *Am. Rev. Respir. Dis.*, 132:182–185, 1985.

Woodring et al., "Pneumothorax ex vacuo", CHEST, 110: 1102–1124 (1996).

* cited by examiner

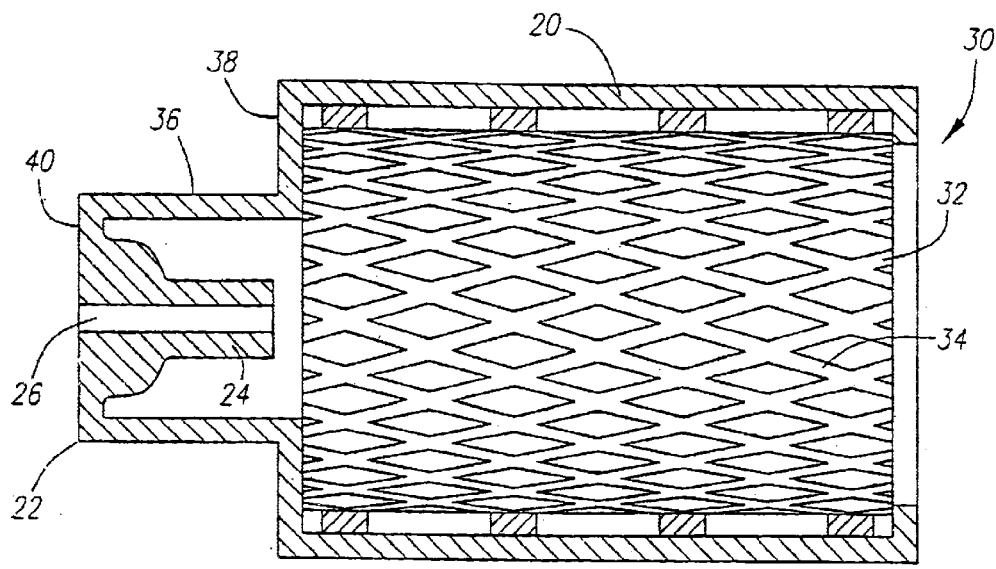
FIG. 3
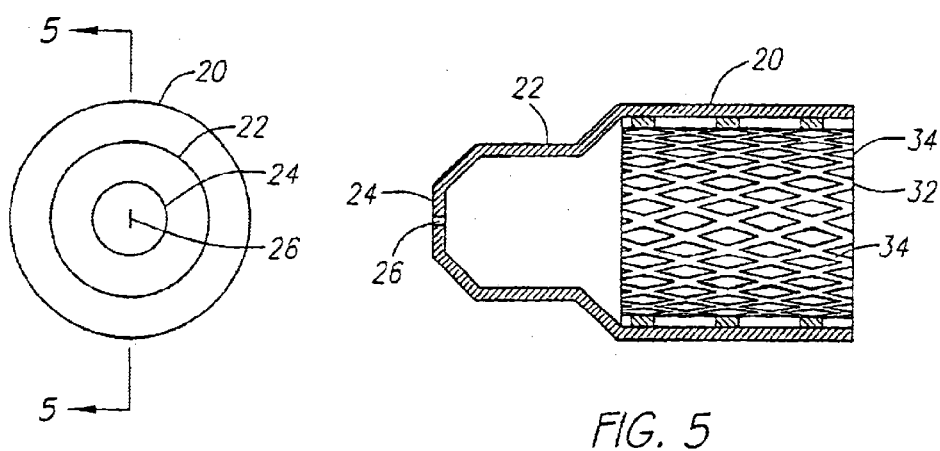
FIG. 4
FIG. 5

BODY FLUID FLOW CONTROL DEVICE

This is a continuing application of U.S. patent application Ser. No. 08/931,552, filed Sep. 16, 1997 and issuing as U.S. Pat. No. 5,954,766, the disclosure of which is incorporated herein by reference.

BACKGROUND OF THE INVENTION

The field of the present invention is valve mechanisms for use in the human body.

Valves play an important role in a number of bodily functions. One such physiologic valve is in the urinary tract. Valve failure in this system leads to urinary incontinence, a significant health issue. Urinary incontinence is estimated to affect some ten million Americans. The full extent of this problem is unknown because less than half of affected adults are believed to actually seek medical attention.

Devices are available to assist in the control of urinary incontinence. Such devices include external valves, valves extending throughout the lower urinary tract and into the bladder, devices extending through long portions of the urethra and implanted protheses as well as injected bulking agents which support the urethral sphincter to enhance operation. Such devices are often inconvenient, uncomfortable and/or require surgical insertion. Other devices are considered overly intrusive.

Native valves are also found in cardiovascular systems. In veins, native venous valves promote one-way flow toward the heart from the periphery. Diseases exist such as venous thrombosis and thrombophlebitis which can render native venous valves incompetent, resulting in edema. Replacement of these native valves with artificial ones could provide substantial health benefits.

The pulmonic valve associated with the heart is yet another native flow control mechanism which can exhibit incompetence either congenitally, through disease or iatrogenically due to treatment of pulmonary stenosis. A one-way valve positioned distal to the native pulmonic valve within the pulmonary artery could be of substantial benefit in overcoming this problem.

SUMMARY OF THE INVENTION

The present invention is directed to a body fluid flow control device which includes an ability to seal about the device in the fluid passageway, a placement and retention format for the device and a valve body capable of either or both a pressure threshold for operation and a one-way flow restriction. The valve body preferably end bulk resilience and a passage therethrough which is closed by that bulk resilience. This may be defined by an elastomeric or other polymeric body with a passage therethrough cut without the removal of material. A single slit, a cross or a star shaped cut are included among the possibilities. One-way flow may be accomplished through a flap or other inhibitor physically impeding flow in one direction or by a configuration of the valve to employ passage pressure to prevent opening.

In a separate aspect of the present invention, such devices as contemplated above are combined with mechanisms to assist in transforming the state of the device from insertion to anchoring.

Accordingly, it is a principal object of the present invention to provide a flow control device for the human body such as for urinary, venous or pulmonic placement. Other and further objects and advantages may appear hereinafter.

BRIEF DESCRIPTION OF THE DRAWINGS

FIG. 3 is a cross-sectional side view of a second flow control device.

FIG. 4 is an end view of a third fluid flow control device.

FIG. 5 is a cross-sectional view taken along line 5—5 of FIG. 4.

DETAILED DESCRIPTION OF THE PREFERRED EMBODIMENTS

Figure 1:
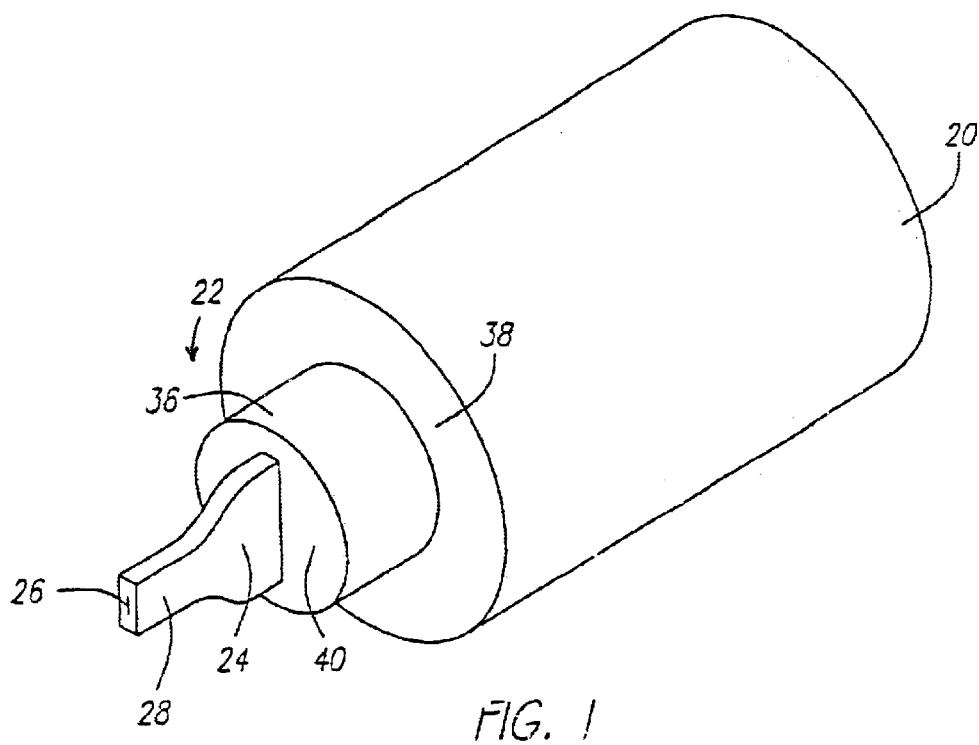
FIG. 1 is a perspective view of a first flow control device.
Figure 2:
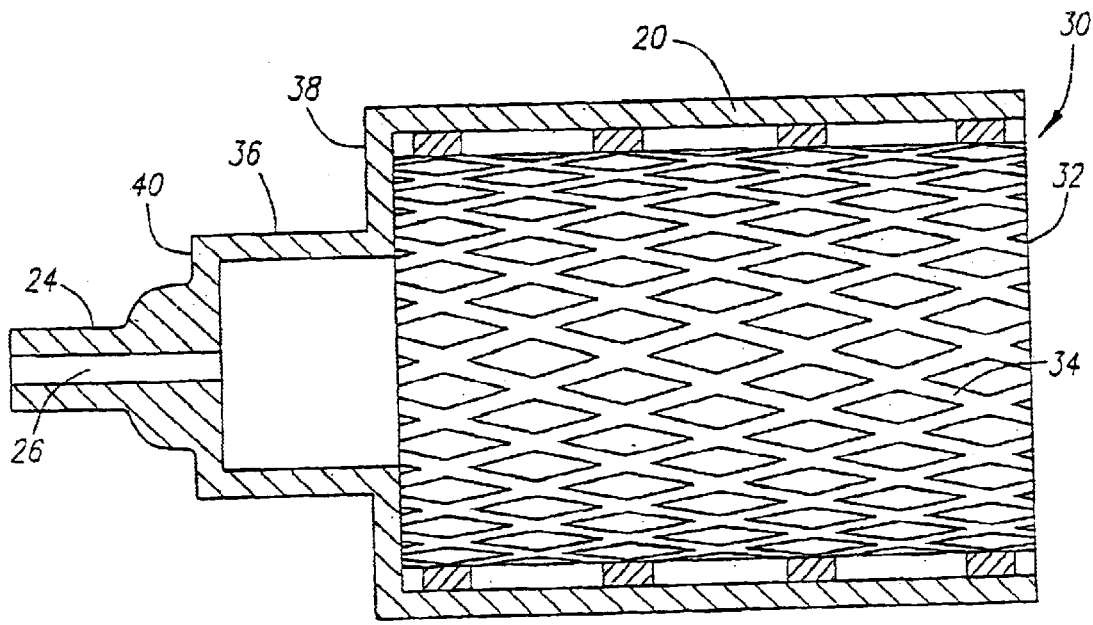
FIG. 2 is a cross-sectional side view of the device of FIG. 1.

FIGS. 1 and 2 illustrate a first fluid flow control device capable of one-way flow, the sealing of a body passageway and pressure actuation. The device includes a resilient seal 20 which, in this first embodiment, includes a cylindrical elastomeric or, more generically, polymeric material capable of sealing within the interior of a body duct or passageway. This resilient seal is shown in this embodiment to be cylindrical but may be tapered through a portion thereof. In either instance, the seal has a substantially circular cross section to fit within the body duct or passageway.

To one end of the seal 20, a valve support 22 extends inwardly from an attachment to the valve body. This valve support 22 preferably provides a barrier to flow through the resilient seal. The support 22 is conveniently formed as one piece with the seal 20.

A valve body 24 is attached to the valve support 22 about the outer periphery of the body 24. The valve body 24 is also of polymeric material and may be most conveniently formed as one piece with the seal 20 and the valve support 22. The body 24 is shown in this first embodiment to define a passage 26 which is shown to be a single slit. The slit 26 extends longitudinally through the valve body. The body of the valve being polymeric and resilient is able to provide bulk resilience to maintain its natural state. As the slit 26 is preferably manufactured without removal of material from the valve body 24, the resilience of the body closes the slit 26 so that no flow can occur. Through empirical testing, an appropriate size of the slit 26 and overall body size and shape of the valve body 24 will define a threshold pressure which may be applied to one end of the valve to cause the slit 26 to open. For purposes of urinary tract control, this opening pressure should be in the range of about 0.2 psi to 3.0 psi. For intervascular placement, the threshold should be from about 0.005 psi to 1.0 psi.

The valve body 24 acts in this embodiment as a one-way valve because of the substantially parallel sides to either side of the slit 26. In the event that flow builds up on the side of the valve with the extending substantially parallel sides 28, the pressure will not only build up at the slit 26, it will also build up on the parallel sides 28 as well. The pressure on the sides will prevent the slit from opening.

A frame, generally designated 30, is located within the peripheral resilient seal 20. This frame 30 is contemplated to be a metallic member having an expanded metal cylinder 32 defined by longitudinally extending elements 34. In this instance, the longitudinally extending elements 34 are interconnected as one construction so as to form the expanded metal cylinder.

The resilient seal forming the peripheral element about the frame 30 to define a seal with the duct or passageway in which the device is placed may be affixed to the frame 30 by any number of conventional means. For example, the frame 30 may be bonded to the resilient seal 20. The resilient seal 20 may be formed through injection molding, blow molding, insertion molding or the like with the frame in place within the mold such that the frame 30 becomes embedded within the seal 20. There may be a physical interlocking through the use of an inwardly extending flange on the open end of the resilient seal 20 to physically retain the frame 30.

The frame 30, being of expanded metal, is capable of being easily stretched to expand from a stable first state to a stable expanded state. The first state, referred to as the insertion state, is contemplated with the overall diameter of the frame 30 and the surrounding resilient seal 20 exhibiting a first diameter. With the frame 30 expanded to what may be termed an anchor state, the resilient seal 20 also expands. In the expanded state, the overall device is intended to fit with interference in the duct or passage. Before expansion, easy insertion is contemplated with clearance.

The construction of this first embodiment provides for the valve support 22 to extend longitudinally in a cylindrical element 36 from an inwardly extending disk element 38. A further inwardly extending disk element 40 extends to the valve body 24. The employment of the cylindrical element 36 between these disk elements 38 and 40 is intended to isolate the valve body 24 from the displacement of the resilient seal 20 as the frame is expanded from an insertion state to an anchor state. Distortion of the valve which may result in a change in the threshold pressure to open the valve may be avoided.

Looking to FIG. 3, a similar view to that of FIG. 2 illustrates a second embodiment. This embodiment differs from the prior embodiment in the redirection of the valve body 24 at the disk 40. With that redirection, the valve body 24 is positioned to face in the opposite direction. In this way, the one-way feature operates to provide flow in the opposite direction relative to the frame 30 and resilient seal 20.

Turning to FIGS. 4 and 5, another embodiment is illustrated. Identical reference numbers are applied to those of the first embodiment to similar structures and functional elements. Presenting a more quantitative description, the wall thickness of the elastomeric polymer defining the resilient seal 20, valve support 22 and valve body 24 is contemplated to be between approximately 0.005" and 0.050". The width of the slit is approximately 0.024" while the outside diameter of the resilient seal 20 is approximately 0.349". The length of this element is contemplated to be approximately 0.60". The frame is cylindrical with an OD in the insertion state of approximately 0.329", a length of approximately 0.304" and a thickness of approximately 0.005" to 0.015". This member is preferably of stainless steel or nitinol. The metallic member in this and each other embodiment is contemplated to be substantially nonreactive with body fluids and the body itself or coated with such a nonreactive material. Other dimensions can also be manufactured depending on the size of the placement.

Figure 6:
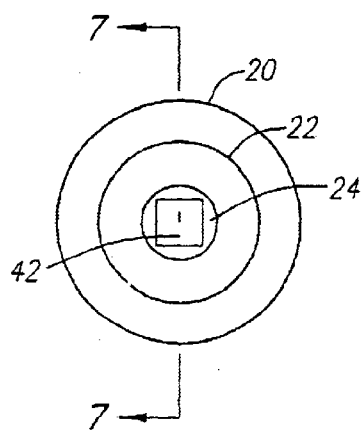
FIG. 6 is an end view of yet another fluid flow control device.
Figure 7:
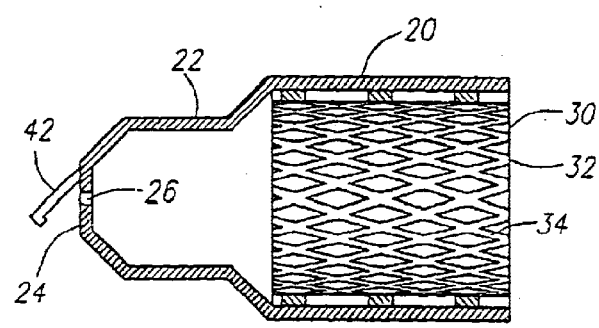
FIG. 7 is a cross-sectional view taken along line 7—7 of FIG. 6.

Turning to the embodiment of FIGS. 6 and 7, substantially the same device is illustrated as in the prior embodiment. Again, the correspondence of reference numerals reflect similar structures and functional features. This device has an added flap 42 overlying the passage 26. The flap 42 is attached by adhesive, bonding or other conventional procedure. The passage 26 may again be a slit as previously described so as to provide a threshold pressure level before opening. If a passageway is presented instead, the device will simply act as a one-way valve.

Figure 8:
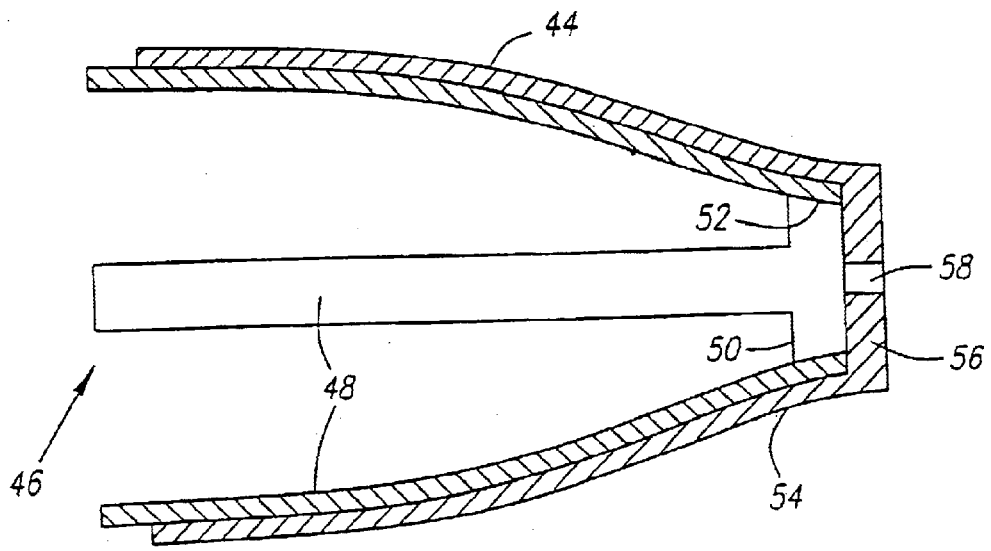
FIG. 8 is a cross-sectional view of yet another fluid flow control device.

Turning to FIG. 8, a different overall exterior configuration is presented as well as a different frame. A polymeric resilient seal 44 is shown to extend over a frame, generally designated 46. The frame 46 includes longitudinally extending elements 48. The elements 48 extend from a conically shaped portion 50 of the frame 46. This conically shaped portion 50 is truncated to provide a wide passageway 52 for operation of the valving mechanism. The resilient seal 44 forms a skirt which extends inwardly to a valve support 54 which is located about the truncated conical portion 50. The valve support 54 and the resilient seal 44 are preferably of the same piece of material. A valve body 56 extends across the passageway 52 in an appropriate thickness to provide the appropriate bulk resilience to accommodate a threshold opening pressure. A passage 58, shown here to be a slit extends through the valve body 56.

Figure 9:
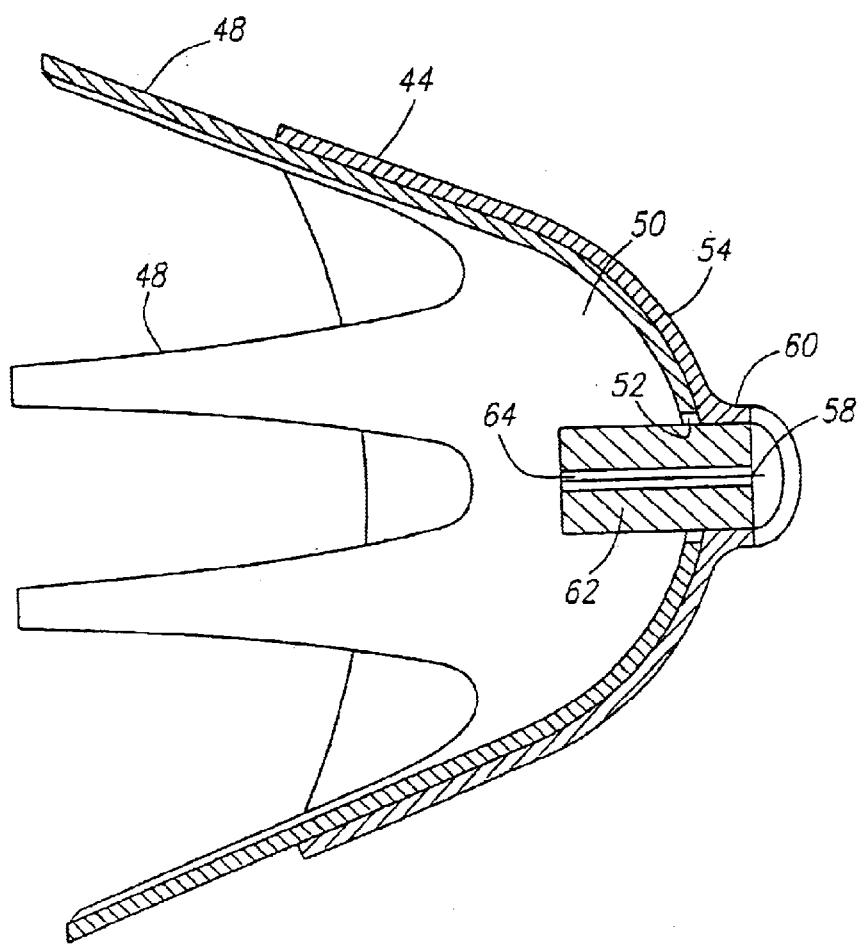
FIG. 9 is a cross-sectional view of yet another fluid flow control device.

Turning to FIG. 9, a device similar to that of FIG. 8 is disclosed. Common reference numerals indicate similar elements and functional features. The resilient seal 44 extends over the longitudinally extending elements as a skirt with the ends of the elements 48 extending outwardly therefrom. A truncated somewhat conical portion 50 actually forming a dome shape extends to a passageway 52. The valve support 54 covers this portion 50. A truncated cone shaped element 60 forms a further part of the valve. It may be part of the same piece of material as the resilient seal 44 and valve support 54. A valve body 62 is shown to be a cylindrical element with a passage 58, shown here to be slits in the form of a cross or star extending longitudinally therethrough.

The length of the valve body 62 establishes that the passage 64 will operate only in expansion and not through bending of the components. Thus, a substantially greater threshold level of pressure is anticipated for this configuration.

Figure 10:
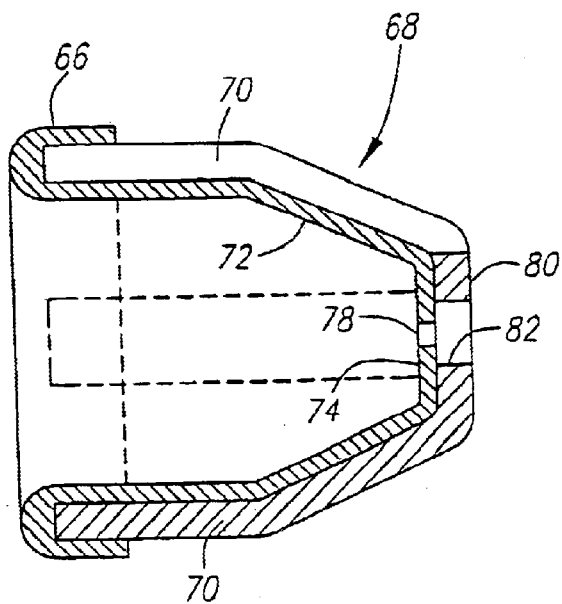
FIG. 10 is a cross-sectional view of yet another fluid flow control device.

FIG. 10 illustrates yet another fluid flow control device. This device includes a resilient seal 66 in the form of a cuff extending about one end of the periphery of the device. The frame 68 is generally on the outside of the valve with longitudinally extending elements 70 extending into the cuff 66. The valve support 72 extends within the frame 68 to a valve body 74 which forms a disk element with a slit 78 therethrough. The frame 68 includes a section in the form of a solid disk 80 with a passageway 82 therethrough. The passageway 82 is substantially larger than the slit 78 in order that it not interfere with the operation thereof. The solid disk 80 also acts to tie together the longitudinally extending element 70 extending out to the cuff 66.

A variety of slits or other mechanisms may be employed to achieve flow through a passage above a preestablished threshold pressure. With thin membranes, a slit or multiple crossed slits can employ a bending component to achieve flow. The bulk resilience is employed more in bending than in radial compression away from the cut or cuts. With longer passageways, radial compression outwardly from the passage provides the controlling mechanism. The thickness of the resilient seal as measured laterally of the slit can be of importance in one-way flow operation. With a thin lateral wall thickness, the pressure surrounding the valve can prevent its opening. Thus, flow would only occur from the side of the valve where pressure cannot accumulate and prevent its opening.

The frame is to be capable of two states, an insertion state and an anchoring state. The anchoring state is larger than the insertion state by the laterally extending resilient elements being outward of the insertion position of these elements when they are in the anchor state.

To achieve these two states, a number of mechanisms may be employed. First, a malleable material can be used. Because the passageways and ducts within the body are quite resilient, large changes in diameter are not required. Consequently, almost any metal is capable of sufficient malleability, particularly if it is employed in an expanded metal state, for example. Reference is made to the embodiment of FIGS. 1 and 2. The choice of metals can become more dependent upon satisfying environmental needs within the body.

Another mechanism which may be employed to accommodate this two-state requirement is spring resilience. The insertion state can be achieved through a preconstraint of the longitudinally extending elements within the elastic range of these elements. Once positioned, the elements can be released to expand into an anchoring state. Constraining tubes or pull wires may achieve the initial insertion state.

Another mechanism which may be used to accomplish both the insertion and the anchor states of the frame is the heat recovery of materials available with alloys such as certain nickel titanium alloys. Preferably the transition temperature of such devices is below body temperature. Under these circumstances, a cool device can be positioned and allowed to attain ambient temperature. The unrecovered state of the frame would be in the insertion position with the longitudinally extending elements in a radially contracted position. Upon recovery, the frame would expand. Another use of this material may be through a heating of the device above body temperature with a recovery temperature zone above that of normal body temperature but below a temperature which may cause burning. The device might be heated electrically or through the modulation of a field.

Figure 11:
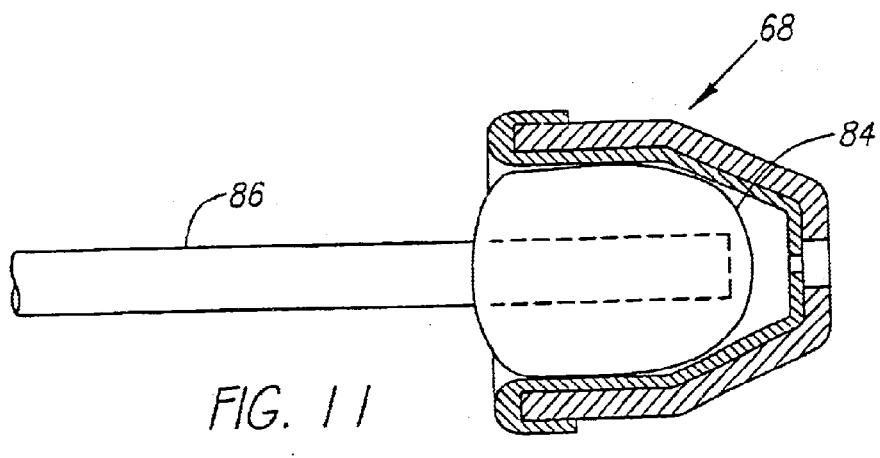
FIG. 11 is a cross-sectional view of the device of FIG. 10 with a balloon expander positioned within the device.

To accomplish a transition from the insertion state to the anchoring state, a variety of devices may be employed. An elongate expander is illustrated in FIG. 11. A balloon 84 is presented at the end of an elongate passage 86 through which pressure may be transmitted. The fluid flow control device can be inserted on the mechanism making up the passage 86 and balloon 84. When in position, the balloon 84 is expanded through the application of pressure to the accessible end of the passage 86. The malleable longitudinally extending elements are bent beyond their yield point into an interfering engagement with the wall of the passageway in the body.

Figure 12:
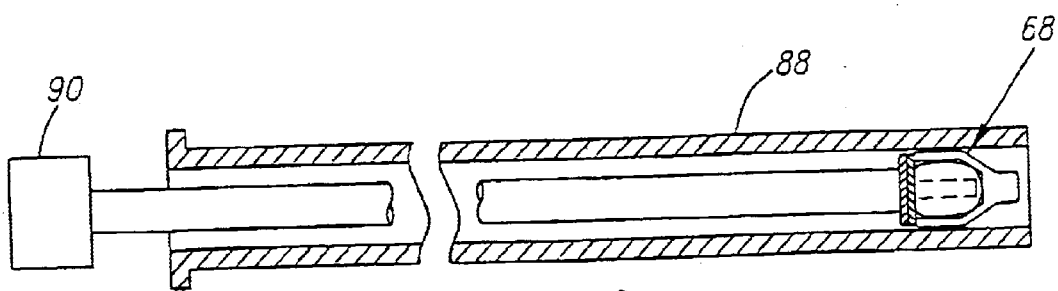
FIG. 12 is a cross-sectional side view of an insertion tool with a fluid flow control device in place.

Another mechanism for providing an elongate expander and insertion tool is illustrated in FIG. 12. The device includes an outer sheath 88 into which is positioned a fluid flow control device which has longitudinally extending elements that are of spring material. The elements are bent such that the frame is radially constricted. The size of the sheath's inner diameter is such that the spring elements are not bent to the point that they exceed the elastic limit. A ram 90 extends into the sheath 88 to force the fluid flow control device from the end of the sheath. As the device its released from the sheath 88, it will naturally expand to the anchored state. This same mechanism may be employed with any of the devices for placement regardless of whether the mechanism for expansion is deformation, heat recovery or resilience. Naturally, the ram 90 can accommodate a heating element or balloon mechanism depending upon the appropriate need.

Figure 13:
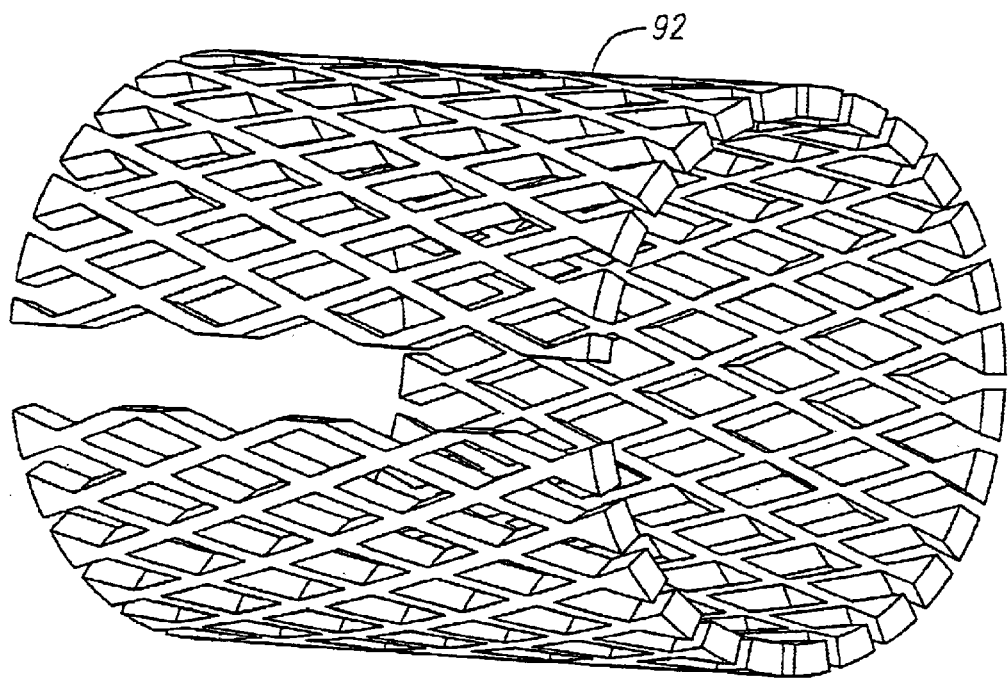
FIG. 13 is a prospective view of another frame.
Figure 14:
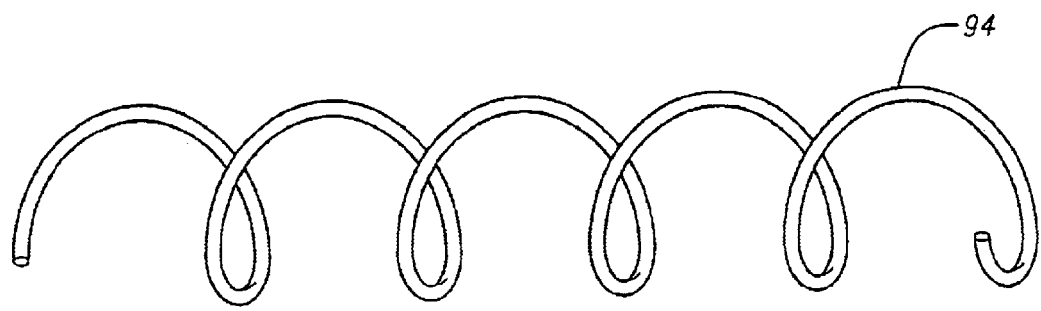
FIG. 14 is a prospective view of yet another frame.

Finally, FIGS. 13 and 14 illustrate two additional forms of the frame which may be employed in place of one of the other frames disclosed. The frame may form a complete cylinder or a rolled sheet 92 as in FIG. 13. A frame which is another alternative is seen in FIG. 14. A longitudinally extending element 94 is formed into a coil. These devices may be of heat recoverable material so as to form an insertion state and an anchor state or be of spring material constrained to a reduced diameter for insertion.

Considering the use of these devices, the thresholds are selected with the appropriate pressures in mind. With incontinence, the threshold pressure is high enough to prevent leakage as normal pressure builds in the bladder. When the bladder is to be voided, abdominal pressure is used. The threshold pressure is also low enough that the abdominal pressure will overcome the resistance and allow flow. Where placement is in the cardiovascular system, minimum resistance to flow in one direction may be designed into the valve. In this application, however, substantial resistance to flow is designed into the valve to eliminate flow in one direction for all pressures contemplated.

Accordingly, a number of improved devices for providing body fluid flow control are disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A body fluid flow control device comprising
   a cylindrically-shaped, resilient seal of substantially annular configuration;
   a frame of substantially circular cross-section extending within at least a portion of the resilient seal and including a passageway extending longitudinally through the frame and at least one longitudinally extending element having an insertion state and an anchoring state, the anchoring state being with the at least one longitudinally extending element outwardly of the insertion state, thereby expanding the portion of the resilient seal within which the frame extends, the passageway being inwardly of the at least one longitudinally extending element;
   a valve body having bulk resilience and a passage therethrough resiliently biased closed by the bulk resilience and communicating with the passageway;
   a valve support about the valve body and attached to the valve body and to the resilient seal, the passage being in communication with the passageway extending longitudinally through the frame.

2. The body fluid flow control device of claim 1, the resilient seal further including a skirt extending at least partially over the at least one longitudinally extending element to form a peripheral seal.

3. The body fluid flow control device of claim 1, the resilient seal further including a skirt extending fully over the frame.

4. The body fluid flow control device of claim 1, the passage having a predetermined fluid opening pressure.

5. The body fluid flow control device of claim 4, the fluid opening pressure being about 0.2 psi to about 3.0 psi.

6. The body fluid flow control device of claim 4, the fluid opening pressure being about 0.005 psi to about 1.0 psi.

7. The body fluid flow control device of claim 1, the passage being a single slit.

8. The body fluid flow control device of claim 1, the resilient seal, the valve body and the valve support being one piece.

9. The body fluid flow control device of claim 1, the at least one longitudinally extending element being heat recoverable with a transition temperature range below a reasonable range of human body temperatures.

10. The body fluid flow device of claim 1, the at least one longitudinally extending element being spring biased towards the anchoring state and being held in the insertion state by preconstraint of the at least one longitudinally extending element by a constraining tube.

* * * * *